United States Patent [19]

Narayanan

[11] Patent Number: 5,389,297
[45] Date of Patent: Feb. 14, 1995

[54] INERT MATRIX COMPOSITION MICROEMULSIFIABLE CONCENTRATE AND AQUEOUS MICROEMULSION

[75] Inventor: Kolazi S. Narayanan, Palisades Park, N.J.

[73] Assignee: ISP Investments Inc., Wilmington, Del.

[21] Appl. No.: 74,076

[22] Filed: Jun. 9, 1993

[51] Int. Cl.$^6$ .............. A01N 25/08; A01N 25/30; B01E 17/16; B01J 13/00
[52] U.S. Cl. .............................. 252/312; 71/DIG. 1; 252/311; 252/314; 252/355; 252/363.5; 424/417; 424/484; 514/937; 514/938; 514/942; 514/965
[58] Field of Search .............. 252/311, 312, 314, 355, 252/363.5; 514/937, 938, 942, 965; 424/417, 484; 71/DIG. 1

[56] References Cited

U.S. PATENT DOCUMENTS

| | | | |
|---|---|---|---|
| 3,535,423 | 10/1970 | Ordas | 71/DIG. 1 |
| 3,920,442 | 11/1975 | Albert et al. | 71/DIG. 1 |
| 4,007,258 | 2/1977 | Cohen et al. | 424/409 |
| 4,540,602 | 9/1985 | Motoyama et al. | 427/213.31 |
| 5,231,070 | 7/1993 | Narayanan et al. | 71/DIG. 1 |
| 5,266,590 | 11/1993 | Narayanan | 514/531 |
| 5,294,644 | 3/1994 | Login et al. | 71/DIG. 1 |
| 5,298,529 | 3/1994 | Narayanan | 514/788 |
| 5,317,042 | 5/1994 | Narayanan | 514/772 |

*Primary Examiner*—Richard D. Lovering
*Attorney, Agent, or Firm*—Walter Katz; Marilyn J. Maue; Joshua J. Ward

[57] ABSTRACT

What is provided herein is an inert matrix composition (IMC), and a microemulsifiable concentrate (MEC) in the form of a free-flowing, high-melting solid, suitable for making an aqueous microemulsion (AME) of an agriculturally active chemical (AAC) with dilution water. The inert matrix composition comprises about 10-50% of a $C_6$-$C_{18}$ alkylpyrrolidone, about 10-50% of an anionic surfactant and about 10-70% of a complexing agent characterized by being an organic compound having a melting point >100° C., a molecular weight $\leq 500$, a water solubility of at least 10% by weight, and being capable of hydrogen-bonding with the alkylpyrrolidone component of the composition. The MEC comprises the IMC and about 1-20% of the agriculturally active ingredient (AAI). Upon dilution with water an AMC is provided having a few ppm to 1% AAI.

9 Claims, No Drawings

INERT MATRIX COMPOSITION MICROEMULSIFIABLE CONCENTRATE AND AQUEOUS MICROEMULSION

BACKGROUND OF THE INVENTION

1. Field of the Invention

This invention relates to a delivery system for an agriculturally active ingredient (AAI), and, more particularly, to an inert matrix composition (IMC), and a microemulsion concentrate (MEC), in the form of a free-flowing, high melting solid suitable for making an aqueous microemulsion (AME) upon admixture with dilution water.

2. Description of the Prior Art

Aqueous microemulsions are favored delivery systems for substantially water-insoluble agriculturally active ingredients because they can accommodate high concentrations of such active materials. Furthermore, they are advantageous from the standpoint of environmental safety, are non-toxic and cost effective, and can be delivered conveniently to the desired site by spraying. Commercial aqueous microemulsions of agriculturally active materials generally are obtained by first providing an inert matrix composition of suitable microemulsifiable materials, adding the agriculturally active ingredient to form a microemulsion concentrate, and then diluting the concentrate with water to form the end-use product. Usually, however, the inert matrix composition is a liquid mixture of solvents and surfactants which must be packaged in cans for shipment to a remote location where it can be mixed with the agriculturally active material. It is understandable that the provision of an inert matrix composition in the form of a free-flowing, high-melting solid would offer advantages that the liquid form does not possess with respect to convenience in packaging and ease of both addition of the agriculturally active material and dilution with water.

Accordingly, it is an object of this invention to provide a delivery system for an agriculturally active ingredient, including an inert matrix composition, in the form of free-flowing, high-melting solids suitable for making a microemulsifiable concentrate and an aqueous microemulsion of the agriculturally active ingredient upon admixture with dilution water.

These and other objects and features of the invention will be made apparent from the following more particular description of the invention.

SUMMARY OF THE INVENTION

What is provided herein is an inert matrix composition (IMC), and a microemulsifiable concentrate (MEC) in the form of a free-flowing, high-melting solid, suitable for making an aqueous microemulsion (AME) of an agriculturally active chemical (AAC) with dilution water. The inert matrix composition comprises about 10–50% of a $C_6$–$C_{18}$ alkylpyrrolidone, about 10–50% of an anionic surfactant and about 10–70% of a complexing agent characterized by being an organic compound having a melting point $>100°$ C., a molecular weight $\leq 500$, a water solubility of at least 10% by weight, and being capable of hydrogen-bonding with the alkylpyrrolidone component of the composition. The MEC comprises the IMC and about 1–20% of the AAI. Upon dilution with water an AMC is provided having a few ppm to 1% AAI.

DETAILED DESCRIPTION OF THE INVENTION

In accordance with the invention, the IMC comprises a higher lactam, i.e. a $C_6$–$C_{18}$ alkylpyrrolidone, e.g. N-octylpyrrolidone, N-isooctylpyrrolidone or N-dodecylpyrrolidone, or mixtures thereof. N-octylpyrrolidone is preferred. The lactam is present in an amount of about 10–50%, preferably 15–40%, and most preferably, 20–30%, by weight of the IMC.

The second component of the IMC is an anionic surfactant which is typified by an alkali metal salt of a $C_8$–$C_{22}$ aliphatic surfactant such as sodium dodecyl sulfate, or an alkyl aromatic sulfate, or sulfonates, ethoxylated derivatives of the above, alkylphenyl ethoxylated phosphate esters, and the like. Sodium dodecyl sulfate is preferred. The anionic surfactant is present in the amount of about 10–50%, preferably 20–45%, and most preferably, 25–35%, by weight of the IMC.

The third component of the IMC is a complexing agent which is characterized by being an organic compound having a melting point of $>100°$ C., a molecular weight of $\leq 500$, a water solubility of at least 10%, and being capable of hydrogen-bonding with the higher alkylpyrrolidone of the IMC. Suitable complexing agents for use herein have a dissociable proton as is present in hydroxy acids, such as lactic or citric acid; amino acids, such as glycine; sugars, such as lactose, sucrose, glucose or fructose; or amides, such as urea. The complexing agent is present in an amount of about 10–70%, preferably 30–60%, and most preferably, 25–50%, by weight of the IMC.

The IMC is provided in the form of a free-flowing, high-melting solid, which is usually a granular, hydroscopic, or crystalline solid having a melting point $>100°$ C.

The MEC of the invention also is a free-flowing solid and is formed by adding the AAI to the IMC, preferably by slurrying the IMC and the AAI with a small amount of water, and spraying, freeze-drying or fluidizing the mixture to form the desired MEC solid. Suitably the MEC includes about 1–20%, preferably 2–15%, and most preferably 3–10%, by weight of an AAI.

The IMC also can be formed by the slurrying techniques used for the MEC.

The aqueous microemulsion usually comprises about 0.01–20 parts by weight of the microemulsion concentrate and about 80–99.99 parts by weight of water, the degree of dilution being determined by the desired concentration of the AAC for the end-use application.

AAC's normally take the form of water-immiscible or oily liquids and/or solids. Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

cyclocompounds:
  6,7,8,9,10,10-hexachloro-1,5,5a,6,9,9a-hexahydro-6,9-methano-2,4,3-benzodioxathiepin-3-oxide benzodioxathiepin-3-oxide carbamates:
  2-isopropyl phenyl-N-methyl carbamate; 2-(1,3-dioxolan-2yl) phenylmethyl carbamate; 2,3-isopropylidine dioxyphenyl methyl carbamate;

animal and plant derivatives:
chlorinated hydrocarbons derived from Southern pine; naturally occurring lactone glycoside;

synthetic pyrethroids:
(±) alpha-cyano-3-phenoxybenzyl (±) cis, trans 3-(2,2-dichlorovinyl)-2,2-dimethyl cyclopropane carboxylate; (±) cyano (3-phenoxyphenyl methyl (±)-4-(difluoromethyoxy) alpha-(1-methylethyl) benzene acetate; D-allethrin permethrin tetramethrin cypermethrin piperonyl butoxide (synergist)

phenoxy compounds and non-phosphate:
2,2-bis (p-methoxy phenyl)-1,1,1, trichloroethane; 1,3,5, tri-n-propyl-1,3,5-triazine-2,4,6 (1H,3H,5H) trione; ethyl (2E, 4E)-3,7,11-trimethyl-2,4-dodeca dienoate; 1-decycloxy 4-[(7-oxa-oct-4-ynyl) ]-oxybenzene;

organic phosphates:
dimethyl phosphate ester of 3-hydroxy-N,N-dimethyl-cis-crotonamide; 2-chloro-1-(2,4-dichloro phenyl) vinyl diethylphosphate; 4-(methyl thio) phenyl dipropyl phosphate;

thiophosphates:
0,0-diethyl-0-4-nitrophenyl phosphorothioate; 0,0-diethyl-0-(2,isopropyl-6- methyl-5-pyrimidinyl) phosphorothioate; 2-diethylamino-6-methyl pyrimidine-4-yl dimethyl phosphorothioate;

dithiophosphates:
0,0-dimethyl phosphorodithioate ester of diethylmrcapto succinate; 0-ethyl-S-phenyl ethyl phosphorodithioate.

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g. triazines, pyridines, pyridazones, picolinic acid, and urea derivates and phosphates. (See *Agricultural Chemicals*, Book II, *Herbicides*, 1986–87 Edition, W. T. Thomson, Thomson Publications, Fresno, Calif. 93791.) Exemplary of the above compounds are:

phenoxy compounds:
2,4-Dichlorophenoxy acetic acid 2,4,5-trichloro phenoxyacetic acid; 4-(2,4-dichlorophenoxy) butyric acid; S-ethyl 2 methyl-4-chlorophenoxy-thioacetate; 2-methyl-4-chloro-phenoxy acetic acid; methyl 5-(2,4-dichloro-phenoxy)-2-nitrobenzoate;

benzoic and acetic acids of phthalic compounds:
3,6-dichloro-o-anisic acid 4-chloro-2-oxo benzothiazolin-3-yl acetic acid; N-1-Naphthyl phthalamic acid;

nitriles and aniline derivatives:
3-5-dibromo-4-hydroxybenzonitrile; α,α,α,-trifluoro-2,6-dinitro-N, N-dipropyl-p-tolinidine; N-(1-ethylpropyl )-2,6-dinitro-3,4-xylidine;

amides, acetamides, anilides:
N,N-diethyl-2-(1-naphthalenyl oxy)-propionamide; 2,6-dimethyl-N-2' methoxy-ethyl-chloro-acetanilide; 3',4'-dichloro-propionanilide; α-chloracetic-N-(3,5,5,-trimethylcyclohexen-1-yl)-N-isopropylamide; 4-benzyl-N-isopropyl trimethyl acetamide;

thiocarbamates:
S-Ethyl dipropyl thiocarbamate;

urea derivatives:
3- (5-tert-butyl-3-isoxazoyl) -1,1-dimethyl urea; N-(2,6-trifluoro-benzoyl)-N'-[2,5-dichloro-4-(1,1,2,3,3,3-hexafluoropropyloxy) phenyl] urea;

pyrrolidone derivatives:
1-(m-trifluoro methyl phenyl)-3-chloro-4-chloromethyl-2-pyrrolidone;

amino acid derivatives:
methyl N-benzoyl-N-(3-chloro-4-fluorophenyl)-DL alarinate; N-chloracetyl-N-(2,6-diethyl phenyl)-glycine ethyl ester;

carbamates:
Isopropyl-m-chlorocarbanilate; 3-Ethoxy (carbonyl aminophenyl)-N-phenyl carbamate;

heterocyclics:
4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methyl ethyl)-5-oxo-1 H-imidazoyl-2yl-3-byridinecarboxylic acid; 2-[3,5-dichlorophenyl)-2-(2,2,2-trichloroethyl) oxinane; Butyl-9-hydro-fluorene-(9)-carboxylate; 2-[1-(ethoxy imino) butyl]-3-hydroxy-5-(2H-tetra hydro thio-pyran-3-yl)-2-cyclohexene-ione; 2-(2 chlorophenyl) methyl-4,4-dimethyl-3-iso oxazolidinone;

phosphates:
0-ethyl-0-(3-methyl-6-nitro phenyl) N-sec-butyl phosphoro thio amidate.

Typical fungicides include (See *Agricultural Chemicals*, Book IV, *Fungicides*, 1989 Revision, W. T. Thomson, Thomson Publications, Fresno, Calif. 93791):

organic compounds:
2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis (2,2,2-trichloro) ethylidene) bis formamide; Tetramethyl thiuram disulfide; 0-Ethyl-S,S,diphenyl-dithiophosphate; 5,10-dihydro-5,10-dioxo naptho (2,3,9)-p-dithiin-2,3-dicarbonitrile; 2-(Thiocyano methyl thio) benzothiazole; α-2-(4-chlorophenyl) ethyl]-α-(1,1-dimethyl ethyl)-1H-1,2,4-triazole-1-ethanol;

morpholines:
N-tridecyl-2,6-dimethyl morpholine; 4-N-dodecyl-2,6-dimethyl morpholine;

Typical fumigants, growth regulators, repellants, and rodenticides include (See *Agricultural Chemicals*, Book III, *Fumigants*, 1988–1989 Revision, W. T. Thomson, Thomson Publications, Fresno, Calif. 93791):

growth regulants:
1,2 Dihydro-6-ethyoxy-2,2,4-trimethylquinoline; (2-chloroethyl) phosphoric acid; 4-[acetamino) methyl ]-2-chloro-N (2,6-diethyl phenyl acetamide; Benzoic acid, 3,6 dichloro-2-methoxy, 2-ethoxy-1-methyl-2-oxo ethyl ester;

repellants:
0,0-dimethyl-0-[(4-methyl thio) -m-tolyl] phosphorothioate; Tetriary butyl-sulfenyl dimethyl dithio carbamate;

seed softener:
2-chloro-6-(trichlomethyl) pyridine; 5-ethoxy-3-trichloromethyl-1,2,4-thiadiazole; N-phenyl-N'-1,2,3-thiadiazol-5-yl urea;

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenoxy) propionic acid,
Common esters of 2,4-dichlorobutyric acid,
Common esters of 2, methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro-1H-azepine-1-carbothioate,
PP 511 0,0-dimethyl-(2-diethylamine 4-methyl-6-pyrimidinyl) carbamate,
PP 211 0,0-diethyl O-(2-diethylamine-4-methyl-6-pyrimidinyl) phosphorocarbamate,
Chlordane
5-Ethoxy-3-(trichlorometyl) -1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamate (RO-NEET®),
Malathion (S-(1,2-dicarboxyethyl)-0,0-dimethyl phosphorodithioate),
Diazinon (0,0-diethyl,0-(2-isopropyl-4-methyl-6-pyrimidinyl) phosphorothioate,
0-Ethyl-S-phenyl-ethylphosphonodithioate (DYFONATE®),
Toxaphene (Octachlorocamphene),
Bromoxynil (3,5-dibromo-4-hydroxy benzonitrile ester of n. octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-triazine) Simazine (2-chloro-4,6,-bis (ethylamino)-s-triazine
Dodine (D-dodecylguanidine acetate)
Thiram (tetramethylthiuram disulfide)
N-(mercaptomethyl)phthalimide s-(o,o dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban ( 4-chloro-2 butynyl m-chlorocarbanilate)
Tricumba 2-methoxy-3,5,6-trichlorobenzoic acid
Trifluralin (2,6-dinitro-N, N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2- (2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2, -Bis (p-methoxyphenyl) -1,1-trichloroethane
PP 781: 4 (2-chloro phenylhydrazono) -3-methyl-5-isoxazolone,
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149:5-n-butyl-2 ethylamino-4-hydroxy-6 methyl-pyrimidine*

* Manufactured by Imperial Chemical Industries Limited

C 63 13 N'-(4 -bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H, 5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy)-phenyl]urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-valerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butyl carbamoyl)-2-benzimidazol carbamic acid, methyl ester (BENLATE ®).

The AME is formed by adding dilution water to the MEC to form an end-use product containing a few ppm to 1% of the AAI. Alternatively, the IM can be added as an activator or spreader-sticker material to the AAI during the final water dilution step.

The advantage of the invention materials over conventional liquid IMCs, or liquid MEC, is that the solid forms of the invention may be packaged for slipping in conventional water-dissolvable bags for processing into the final-use, fully diluted AME formulations.

The invention will now be described in more detail with reference to the following examples, as summarized in the Table below.

TABLE
FREE-FLOWING, HIGH-MELTING SOLID INERT MATRIX COMPOSITION OF INVENTION

| Component | 1 (Control) | 2 | 3 | 4/5 | 6/9 | 7 | 8 | 10 |
|---|---|---|---|---|---|---|---|---|
| Lactam | | | | | | | | |
| N-Octylpyrrolidone | 40.6 | 20.3 | 20.3 | 20.3 | 20.3 | 30.5 | 30.5 | 25.7 |
| Anionic Surfactant | | | | | | | | |
| Sodium dodecyl Sulfate | 59.4 | 29.7 | 29.7 | 29.7 | 29.7 | 44.5 | 44.5 | 10.9 |
| Complexing Agent | | | | | | | | |
| Fructose | — | 50.0 | — | — | — | — | — | — |
| Glucose | — | — | 50.0 | — | — | — | — | — |
| Lactose | — | — | — | 50.0 | — | 25.0 | — | — |
| Urea | — | — | — | — | 50.0 | — | 25.0 | 63.4 |
| | 100.0 | 100.0 | 100.0 | 100.0 | 100.0 | 100.0 | 100.0 | 100.0 |
| Physical Form | Paste | Solid | Solid | Solid | Solid | Solid | Solid | Solid |
| Melting Point (°C.) | — | 100–120° | 107–128° | 151° | 112–114° | >100° | — | — |

EXAMPLE 1 (Control)

43.26 g. (0.15 mole) of sodium dodecyl sulfate (SDS) solid was intimately mixed with 29.55 g. (0.15 mole) of N-octylpyrrolidone (NOP). The resulting paste was homogenized with stainless steel ball bearings on a jar mill over a period of 18 hours. The composition was still a paste in its average composition. NOP: 40.6%; SOS: 59.4%.

EXAMPLE 2

5.0 g. of the paste of Example 1 was admixed in a jar mill with 5.00 g. of fructose. A hydroscopic solid was obtained with average compositions:

| NOP: | 20.31 |
|---|---|
| SDS: | 29.7% |
| Fructose: | 50.0% |
| | 100.0% |

This solid melted around 120° C. with softening starting around 100° C. The sample dissolved completely at 1% in water with less than 60 inversions in a long nesslers tube (~1 cm dia, ~18 cm long).

EXAMPLE 3

Example 2 was repeated using 5.0 g. of glucose. The jar milled sample was a hygroscopic solid-m.pt. ~128° C. with softening starting at 107° C. It dissolved at 1% in water in 60 inversions.

EXAMPLE 4

Example 2 was repeated replacing 5.0 g. fructose with 5.0 g. lactose. The jar-milled product was a high melting solid with m.pt. 158° C. Dissolved at 1% in water in <60 inversions.

EXAMPLE 5

29.7 g. solid SDS, 50 g. β-D-lactose, 20.3 g. NOP and 50.0 g. deionized water was charged in a jar. The slurry was blended in a ball mill with stainless steel balls for 1 hour. The homogenized product was freeze-dried over 24 hours to a free-flowing, white powder with m.pt. 149°–151° C.

EXAMPLE 6

Example 5 was repeated replacing β-D lactose with urea to produce a white powder with, m.pt. 112°–114° C. This product dissolved at 1% in water with <60 inversions.

EXAMPLE 7

Example 5 was repeated with the following initial charge: 44.6 g. SDS, 30.5 g. NOP, 25 g. β-D-lactose, 50 ml deionized water. The slurry was blended in a ball mill with stainless steel balls for 1 hour followed by freeze-drying overnight. The product was a free-flowing, powder.

EXAMPLE 8

Example 6 was repeated with the following initial charge:

44.5 g. SDS, 30.5 g. NOP, 25 g. urea and 50 ml deionized water. The product was a free-flowing, high melting solids.

EXAMPLE 9

Example 6 was modified as follows. The initial charge was stirred in a mechanical stirrer, and the slurry was directly freeze-dried overnight to produce a crystalline solid. The residual moisture was <1%.

EXAMPLE 10

Example 9 was repeated with the following initial charge. NOP: 20.3 g., as 29% aqueous solution of SDS 29.7 g, NOP: 20.3 g. of urea, 50.0 g. deionized water 50 ml. The product then was freeze-dried as above.

EXAMPLE 11

The inert matrix compositions of Examples 4/5, 6/9, 7 and 8 were used to load agriculturally active ingredients at 1-3% levels. Accordingly, technical grade carbaryl was dry mixed at 1-3 parts with the above inert compositions to make up 100 parts of the resulting compositions. The compositions of Examples 6/9, 7 and 8 produced free-flowing solids whereas composition of Example 4/5 produced sticky, waxy solids.

EXAMPLE 11A

The product obtained from 97-99% of composition 6/9 and 1-3% carbaryl were further evaluated for their rate of dispersion in water and the stability of the resulting dispersions. Accordingly, the solids were dispersed in dilution water to produce a 0.1 to 0.3% AAI level in the final diluted samples. All the diluted samples formed clear, single phase systems with less than 100 inversions, with minute solids at the bottom. The clear dispersions were found to contain 90+% carbaryl (UV spectral analysis) even after storage for 30 days.

For example: 97 parts of composition of 8, Ex. 6/9 and 3 parts of carbaryl produced the following composition I.

| Composition I | |
|---|---|
| Tech carbaryl | 3.0% |
| NOP | 19.7% |
| SDS | 28.8% |
| Urea | 48.5% |
| Total | 100.0% |

Composition I was dispersed in water at three levels. 10, 6.7 parts and 3.35 parts of I were dispersed in 90, 93.3, and 96.65 parts of water, respectively. All the samples dispersed completely in less than 60 inversions producing a clear single phase system. The % recovery of the carbaryl as determined via UV spectral analysis showed >90% recovery even after standing for 30 days.

Other samples from Example 11 produced similar results, however requiring 60-200 inversions to disperse.

EXAMPLE 12

The composition I shown in Example 11A, was also prepared in a direct manner. Accordingly, Composition I was mixed with 50 g. deionized water, sonicated for 1 hour, and freeze-dried. The freeze-dried solid contained about 3% carbaryl dispersed in water at 0.1-0.3% carbaryl in a clear single phase system with recovery >90% after storage for 1 month.

What is claimed is:

1. An inert matrix composition in the form of a free-flowing, high melting solid suitable for making a solid microemulsion concentrate upon admixture with an agriculturally active ingredient which comprises, by weight of the composition, about 10-50% of a $C_6$-$C_{18}$ alkylpyrrolidone, about 10-50% of an anionic surfactant and about 10-70% of a water-soluble, high melting organic compound containing a dissociable proton which can complex with said pyrrolidone, a melting point of >100° C. a molecular weight of $\leq 500$, and a water solubility of at least 10%, which is selected from the group consisting of hydroxy acids, amino acids, sugars and amides.

2. An inert matrix composition according to claim 1 wherein said $C_6$-$C_{18}$ alkylpyrrolidone is N-octylpyrrolidone.

3. An inert matrix composition according to claim 1 wherein said anionic surfactant is sodium dodecyl sulfate.

4. An inert matrix composition according to claim 1 comprising 15-40% of N-octylpyrrolidone and 20-45% of sodium dodecyl sulfonate and 30-60% of said organic compound.

5. An inert matrix composition according to claim 1 wherein said organic compound is urea, fructose, glucose, lactose or sucrose.

6. An inert matrix composition according to claim 1 comprising about 20-30% by weight of said $C_6$-$C_{18}$ alkylpyrrolidone, about 25-35% by weight of said anionic surfactant and about 25-50% by weight of said organic compound.

7. An inert matrix composition according to claim 1 which is a granular to crystalline solid having a melting point of about 110°-160° C.

8. A solid microemulsifiable concentrate comprising the inert matrix composition of claim 1 and 1-20% by weight of an agriculturally active ingredient.

9. An aqueous microemulsion comprising the solid microemulsifiable concentrate of claim 8 and dilution water in an amount sufficient to reduce the concentration of the agriculturally active ingredient to between a few ppm and 1% by weight.

* * * * *